United States Patent
Shah

(10) Patent No.: US 10,089,492 B2
(45) Date of Patent: Oct. 2, 2018

(54) PATIENT NAVIGATION AND SITUATIONAL AWARENESS DERIVED THROUGH CONTEXT-SENSITIVE INFORMATION BLOCKS DELIVERY

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 159 days.

(21) Appl. No.: 15/163,662

(22) Filed: May 24, 2016

(65) Prior Publication Data

US 2016/0350554 A1 Dec. 1, 2016

Related U.S. Application Data

(60) Provisional application No. 62/166,103, filed on May 25, 2015.

(51) Int. Cl.
| | |
|---|---|
| *H04L 29/06* | (2006.01) |
| *G06F 21/62* | (2013.01) |
| *G06Q 10/06* | (2012.01) |
| *G16H 10/60* | (2018.01) |

(52) U.S. Cl.
CPC ..... *G06F 21/6245* (2013.01); *G06Q 10/0633* (2013.01); *G16H 10/60* (2018.01)

(58) Field of Classification Search
CPC .............. G06F 21/6245; G06F 19/322; G06Q 10/0633
See application file for complete search history.

(56) References Cited

U.S. PATENT DOCUMENTS

| | | |
|---|---|---|
| 8,127,000 B2 | 2/2012 | Wenig et al. |
| 8,335,848 B2 | 12/2012 | Wenig et al. |
| 2012/0246122 A1* | 9/2012 | Short ............ G06Q 10/06 707/690 |

FOREIGN PATENT DOCUMENTS

| | | |
|---|---|---|
| WO | 2014048851 A2 | 4/2014 |
| WO | 2014059257 A2 | 4/2014 |

* cited by examiner

*Primary Examiner* — Tri M Tran
(74) *Attorney, Agent, or Firm* — Rahman LLC

(57) ABSTRACT

A surveillance system for monitoring of Electronic Medical Record (EMR) application navigation through a plurality of navigation interfaces of an EMR application. The system includes an EMR system that includes the EMR application. The system includes a context-sensitive engine that includes an agent device to record EMR application navigation data in real time and contextual data comprising application sensitive, user sensitive and context sensitive data. The system includes an information management server to facilitate serving of information blocks to the EMR system from a plurality of distributed databases in real-time. The system includes a processing that analyzes the plurality of navigation interfaces associated with the EMR application during a workflow event, maps the analyzed navigation data and the contextual information with actual information pre-stored in a separate database connected with the EMR system, and determine an inconsistency in a navigation workflow during the workflow event based on the mapping.

15 Claims, 10 Drawing Sheets

PATIENT NAVIGATION AND SITUATIONAL AWARENESS DERIVED THROUGH CONTEXT-SENSITIVE INFORMATION BLOCKS DELIVERY

CROSS-REFERENCE TO RELATED APPLICATIONS

This application claims the benefit of U.S. Provisional Application No. 62/166,103, filed on May 25, 2015 and entitled "Patient Navigation and Situational Awareness Derived Through Context-Sensitive Information Blocks Delivery," the complete disclosure of which, in its entirety, is hereby incorporated by reference.

BACKGROUND

Technical Field

The embodiments herein generally relate to data management, and more particularly to integration and tracking of medical data across electronic medical record systems for specific purposes.

Description of the Related Art

Electronic Medical Records (EMR) systems create and maintain all patient data electronically. The system captures patient data, such as patient complaints, lab orders, medications, diagnoses, and procedures, at its source at the time of entry using a graphical user interface. Authorized healthcare providers can access, analyze, update and electronically annotate patient data even while other providers are using the same patient record. The system also permits instant analysis of patient data to identify relationships among data elements. The system also includes a capability to access reference databases for medical consultation.

However, patient medical records are highly sensitive documents, and it is crucial to maintain confidentiality of the records and allow only qualified people to have access to them. Physicians and hospitals are subject to sanctions for any violations of patient-physician confidentiality. For example, if the database is to be used for data mining, the identity of the patients must be protected from researchers seeking information. Even the system administrator of the database should be prevented from accessing the medical records stored in the database. If individual patients are allowed access to the database, they must have access to only their own medical record.

In view of the above, there is a need of a system and method to perform surveillance of access to the medical records by patients and health care providers and thus provide enhanced security and confidentiality based on access tracking.

SUMMARY

An embodiment herein provides a computer-implemented surveillance system for monitoring and surveillance of Electronic Medical Record (EMR) application navigation through a plurality of navigation interfaces of an EMR application. The system comprises an EMR system that includes the EMR application. The EMR system is configured to execute computer executable instructions to manage medical records electronically. The system further includes a context-sensitive engine operatively deployed at a front-end of the EMR system. The context-sensitive engine includes an agent device to record EMR application navigation data in real time and contextual data comprising application sensitive, user sensitive and context sensitive data. The agent device is operatively and communicatively connected with the EMR system. The context-sensitive engine further includes an installable computer-executable agent file to allow configuration and setup of the agent device. The system further includes an information management server communicatively connected with the EMR system to facilitate serving of information blocks to the EMR system from a plurality of distributed databases in real-time, wherein each of the plurality of distributed databases are communicatively connected with the EMR system through the information management server. The delivery of the information blocks is based on the contextual information. The system further includes a transceiver to transmit the navigation data and the contextual data from the agent device to the information management server. The system further includes a processing circuit included within or communicatively coupled with the information management server. The processing circuit analyzes the plurality of navigation interfaces associated with the EMR application during a workflow event to generate a signal indicative of analyzed navigation data, maps the analyzed navigation data and the contextual information with actual information pre-stored in a separate database connected with the EMR system, and determine an inconsistency in a navigation workflow during the workflow event based on the mapping. The actual information may signify events occurrences within an environment. The system further includes a notification device to report the inconsistency to the EMR system. The notification device generates an electric signal comprising a computer executable file signifying the inconsistency in the navigation workflow during the workflow event, transmits the electric signal, in a network comprising a plurality of communicatively linked data communication devices, converts the electric signal into a plurality of pixels, and displays the plurality of pixels on a display unit to indicate the navigation data and the inconsistency therein.

An embodiment herein provides a computer-implemented surveillance method for monitoring and surveillance of EMR application navigation through a plurality of navigation interfaces of an EMR application. The method includes recording EMR application navigation data in real time by an agent device installed at a front-end of the EMR application and recording contextual data comprising application sensitive data, user sensitive data, and context sensitive data by the agent device. The agent device is operatively and communicatively connected with the EMR system. The method further includes transmitting the navigation data and the contextual data from the agent device to the information management server, analyzing the plurality of navigation interfaces associated with the EMR application during a workflow event by a processing circuit to generate a signal indicative of analyzed navigation data, and mapping the analyzed navigation data and the contextual data with actual information pre-stored in a separate database connected with the EMR system. The actual information signifies events occurrences within an environment. The method may further include determining an inconsistency in a navigation workflow during the workflow event based on the mapping, reporting the inconsistency to the EMR system through a notification device. The reporting includes generating an electric signal comprising a computer executable file signifying the inconsistency in the navigation workflow during the workflow event, transmitting the electric signal, in a network comprising a plurality of communicatively linked data communication devices, converting the electric signal into a plurality of pixels, and displaying the plurality of pixels on a display unit to indicate the navigation data and the inconsistency therein.

BRIEF DESCRIPTION OF THE FIGURES

In the drawings, like numerals describe similar components substantially throughout the several views. The drawings illustrate generally, by way of an example, but not by a way of limitation, various embodiments.

DETAILED DESCRIPTION

Figure 1:
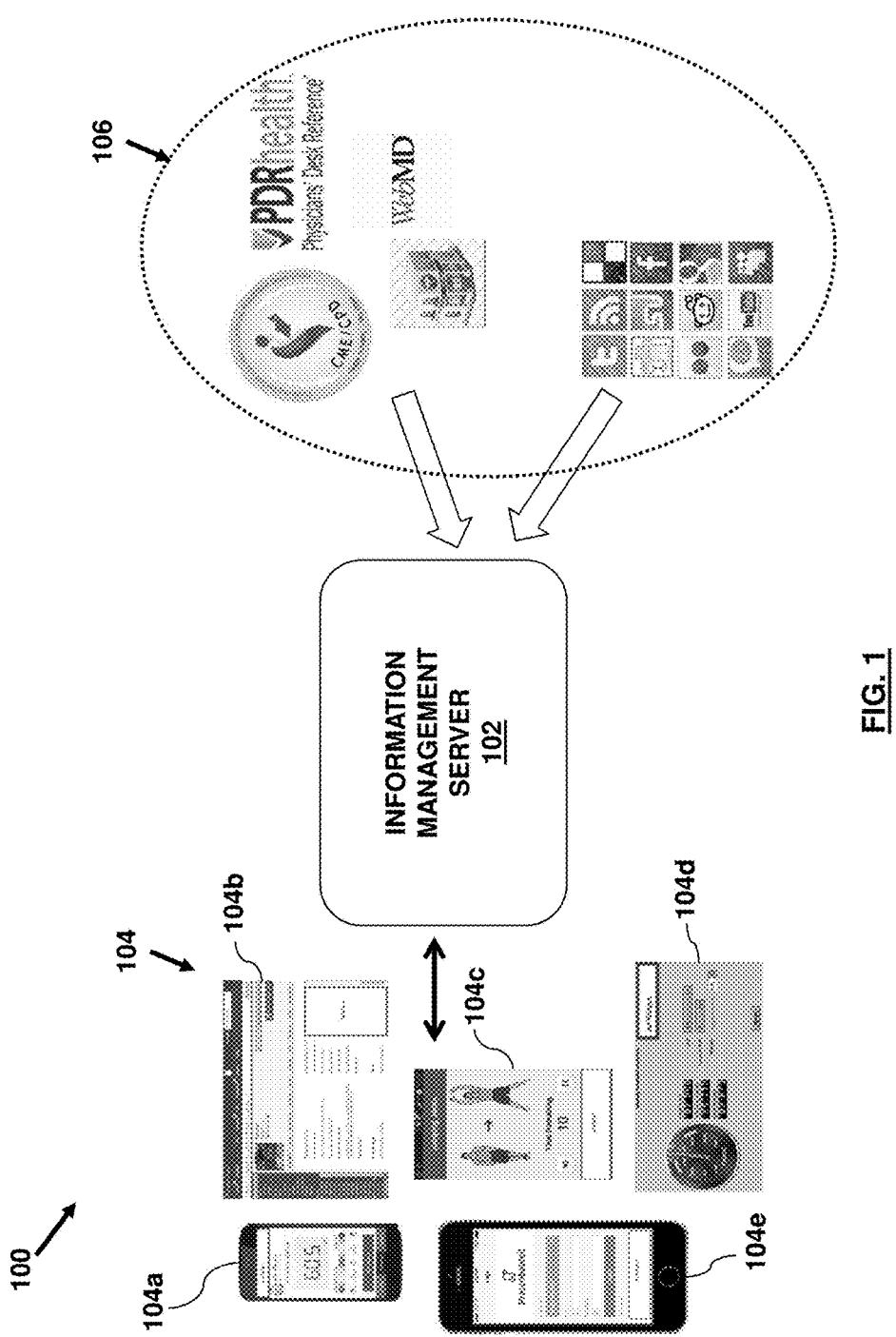
FIG. 1 illustrates architecture for managing and delivering context-based information blocks in accordance with an embodiment herein.

In the following detailed description, reference is made to the accompanying drawings that form a part hereof, and these are shown by way of illustrating specific embodiments herein that may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

In this document, the terms "a" or "an" are used, as is common in patent documents, to include one or more than one. In this document, the term "or" is used to refer to a "nonexclusive or" unless otherwise indicated. Referring now to the drawings, and more particularly to FIGS. 1 through 10, where similar reference characters denote corresponding features consistently throughout the figures, there are shown preferred embodiments.

Figure 2:
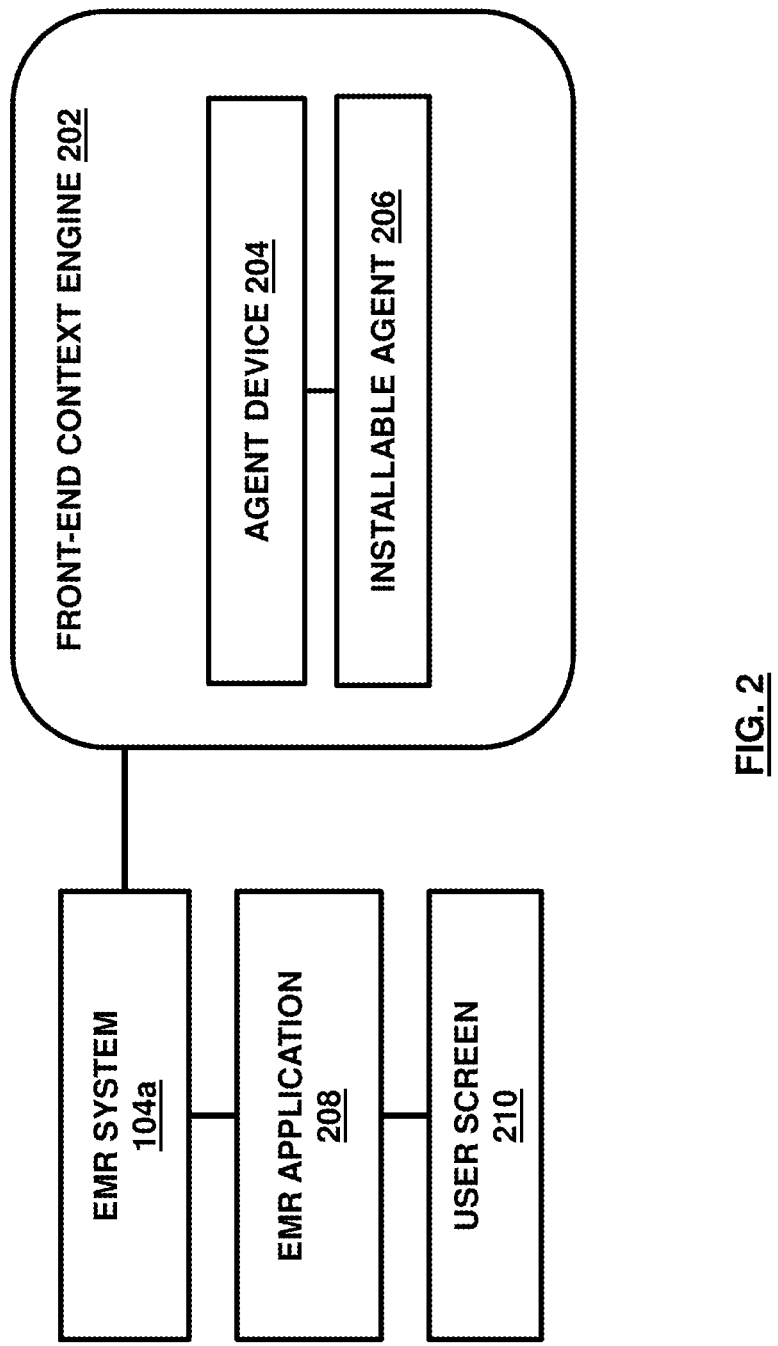
FIG. 2 illustrates an EMR system including or communicatively and/or operatively coupled with a context engine in accordance with an embodiment herein.

FIG. 1 illustrates electronic architecture 100 for managing and delivering context-based information blocks in accordance with an embodiment herein. The architecture 100 includes an information management server 102 that integrates a plurality of discrete and independent electronic medical record systems (EMR systems) 104a, 104b, 104c, 104d, and 104e (together referred to as 104) with information sources 106 located at third party systems and serves the EMR systems 104 with a plurality of context-based information blocks derived from the information sources 106 based on context evaluations performed by a front-end context engine (also referred to as context engine interchangeably without limitations) such as 202 (shown in FIG. 2) deployed at each of the EMR systems 104. FIG. 2, with reference to FIG. 1, illustrates the EMR system 104a including or communicatively and/or operatively coupled with the context engine 202. The front-end context engine 202 (interchangeably referred to as context engine 202) includes an agent device 204 that may be coupled communicatively and operatively with the EMR system 104a. Similar agent devices and context engines may be coupled with or deployed at other EMR systems 104. The agent device 204 may be operated by deploying an installable agent 206 at the EMR system 104a. In an example, the installable agent 206 may be integrated with the EMR system 104a by an external institution. In an example, the installable agent 206 may be defined in the form of a browser plugin installed by a user himself.

Referring back to FIG. 1 in conjunction with FIG. 2, the architecture 100 and the context engine 202 and other components are discussed hereafter.

The EMR systems 104 may be capable of executing several tasks to manage medical records electronically through automated, semi-automated or manual processes. The EMR systems 104 may capture and analyze patient data quickly and efficiently. The EMR systems 104 may capture patient data at its point of source or at a point of care or at the time of entry to provide an audit trail of the entire patient data or medical records. The EMR systems 104 may enable authorized healthcare providers to access and update patient files through computing devices. The EMR systems 104 may permit healthcare providers, such as physicians or nurse practitioners, to electronically annotate the patient data or medical records. A healthcare provider may, for example, acknowledge reviewing patient data, provide instructions, such as prescriptions for medication to administer to a patient, and approve recommendations for treatment by other providers, all by electronically annotating a patient's record. In addition, authorized healthcare providers may access a record while other providers may use the same record allowing for real-time collaboration. The availability of electronic medical records may permit instant, sophisticated analysis of the patient data. The EMR systems 104 may enable analysis of the patient data by providing access to databases for diagnosis, procedures and medication.

The information sources 106 may be hosted by applications such as websites or electronic applications or mobile applications or computing machines associated with third party companies or third party vendors (or merely third parties for simplicity of description). The information sources 106 may be made available as the information blocks based on context data analysis, application data analysis, and user data analysis by the information management server so as to generate necessary information presentable on the user screen in the form of the information blocks by the information management server through the agent device 204.

A healthcare provider may work on a patient in an EMR application 208 provided by an EMR system such as the EMR system 104A for performing tasks such as analyzing patient demographics, writing prescriptions, and the like. The information management server 102 may provide the information blocks to be displayed in the EMR application 208 of the EMR system 104a. The agent device 204 may record activities performed in the EMR application 208. The agent device 204 deployed at the EMR system 104a may know in real time at the front-end what a user is doing. The user may be a clinician, physician, technician, patient, nurse or any other healthcare provider or even any user other than healthcare provider. The agent device 204 may be configured to record the type of user associated with the EMR application 208 at a specific point of time such as in association with time elements. The agent device 204 may also be configured to record type of data being viewed by the user or displayed at the user screen 210 in context. The agent device 204 may allow knowing in real-time the EMR system 104a that works completely independently of other EMR systems 104. The agent device 204 may be capable of recording information that is context sensitive, application sensitive, and user sensitive (such as patient sensitive or healthcare provider sensitive).

Figure 3:
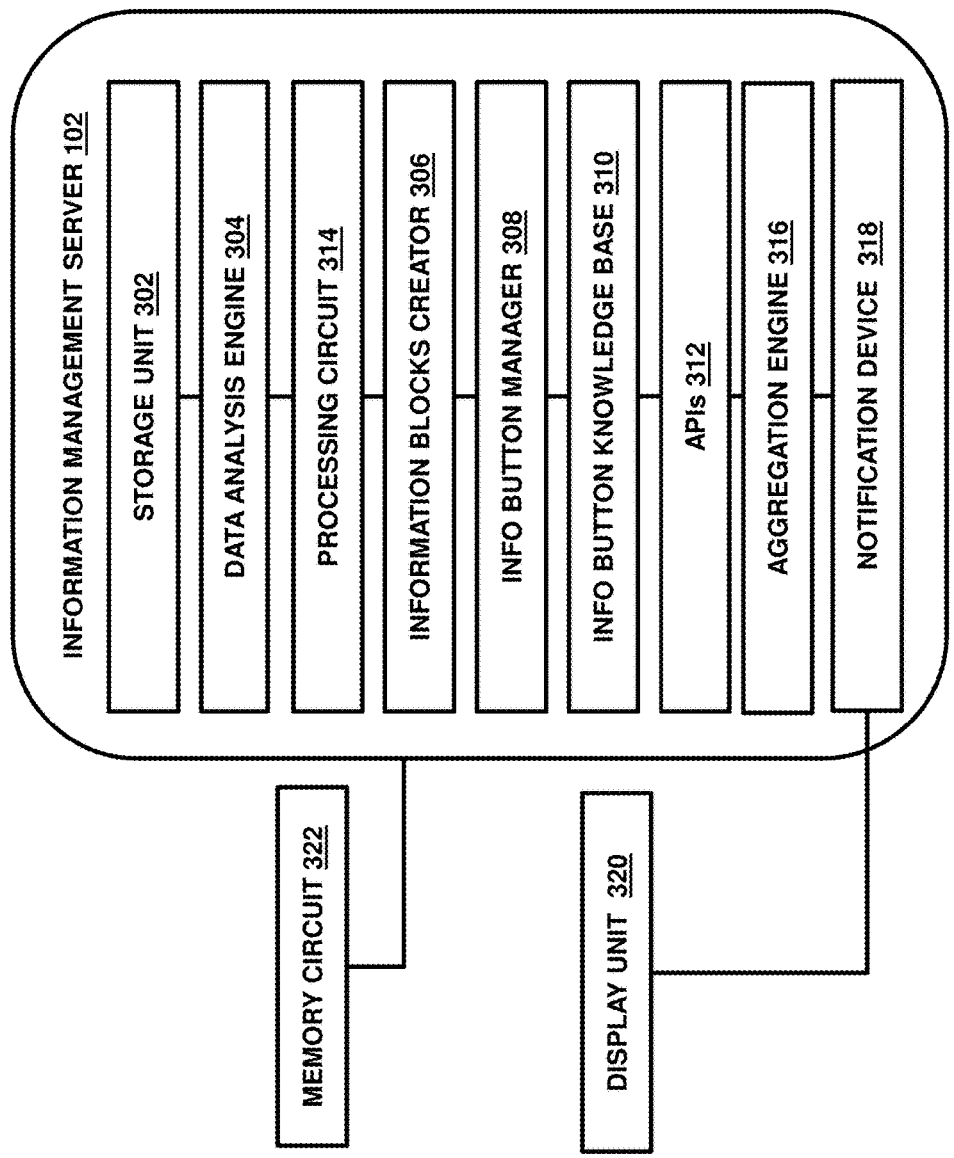
FIG. 3 illustrates an information management server in accordance with an embodiment herein.

The recorded context sensitive, application sensitive, and user sensitive information (together referred to as contextual data or information or context sensitive data or information or contextually sensitive data or information) may be supplied to the information management server 102 for further processing of the information and generating and delivering the information blocks to the EMR systems 104 as discussed later. The contextual data may change with time and may also be different for different EMR applications of the different EMR systems 104. Accordingly, as shown in FIG. 3 and discussed later, the information management server 102 includes a data storage unit 302 to maintain time elements and EMR data elements that may be dependent on one another. The information management server 102 is discussed herein below in conjunction with FIGS. 1 and 2.

FIG. 3, with reference to FIGS. 1 and 2, illustrates the information management server 102 in accordance with an embodiment herein. The information management server 102 may include the storage unit 302 to maintain time elements and EMR data elements in association with the EMR system 104a as obtained from the agent device 204 deployed at the front-end of the EMR system 104a. For example, the time elements and the EMR data elements may be stored separately for each of the EMR systems 104. The time elements may be indicative of specific time information associated with the EMR application 208 of the EMR system 104a. The EMR data elements may be indicative of specific medical or other data displayed on the user screen such as the user screen or interface 210 through the EMR application 208 and may be dependent on the time elements such that the time elements and the EMR data elements together provide information about what is being displayed at a particular time on the user screen 210 through the EMR application 208.

The information management server 102 may access the information sources 106 hosted by information consumers and generate the information blocks based on the context sensitive, the application sensitive and the user sensitive data (hereafter referred together as contextual data) displayed on the user screen 210 of the EMR application 208 associated with a healthcare provider or other user such as a patient.

The information management server 102 may include a data analytics engine 304, an information blocks creator 306, an information button manager 308, and an information button knowledge base 310. The data analytics engine 304 may process the information received from the agent device 204 associated with the EMR system 104a. The information blocks creator 306 may connect with the information sources 106 and generate the information blocks in relation with the contextually sensitive information received from the agent device 204 so that the information blocks represent in one or more ways of sensitivity a correlation with the information recorded by the agent device 204. The information management server 102 may include a set of APIs 312. The information management server 102 may allow custom applications through the use of APIs 312. The info button manager 308 and the info button knowledge base 310 may facilitate a user to be directed to a knowledge source that may allow the user to access detailed content related to the information blocks presented to the user. The workflow of the EMR system 104a may be maintained while the user is directed to the content. The info button knowledge base (or information button knowledge base) 310 configures a widget presentable on the EMR application 208 along with an information block such that the information block presents a limited information to the EMR application 208 and the widget facilitates redirection to a detailed view of the information at a source web page from where the information contained within the information block is aggregated by the information blocks creator 306.

The information management server 102 may include an aggregation engine 316 to aggregate a plurality of information pieces from a plurality of distributed databases containing a variety of information types from the information sources 106. In an example, the information blocks are configured as real time information widgets presentable on a display of the EMR system 104, wherein the presentable real time information widgets are configured based on the plurality of information pieces aggregated by the aggregation engine 316 and the contextual data obtained from the agent device 204.

Figure 4:
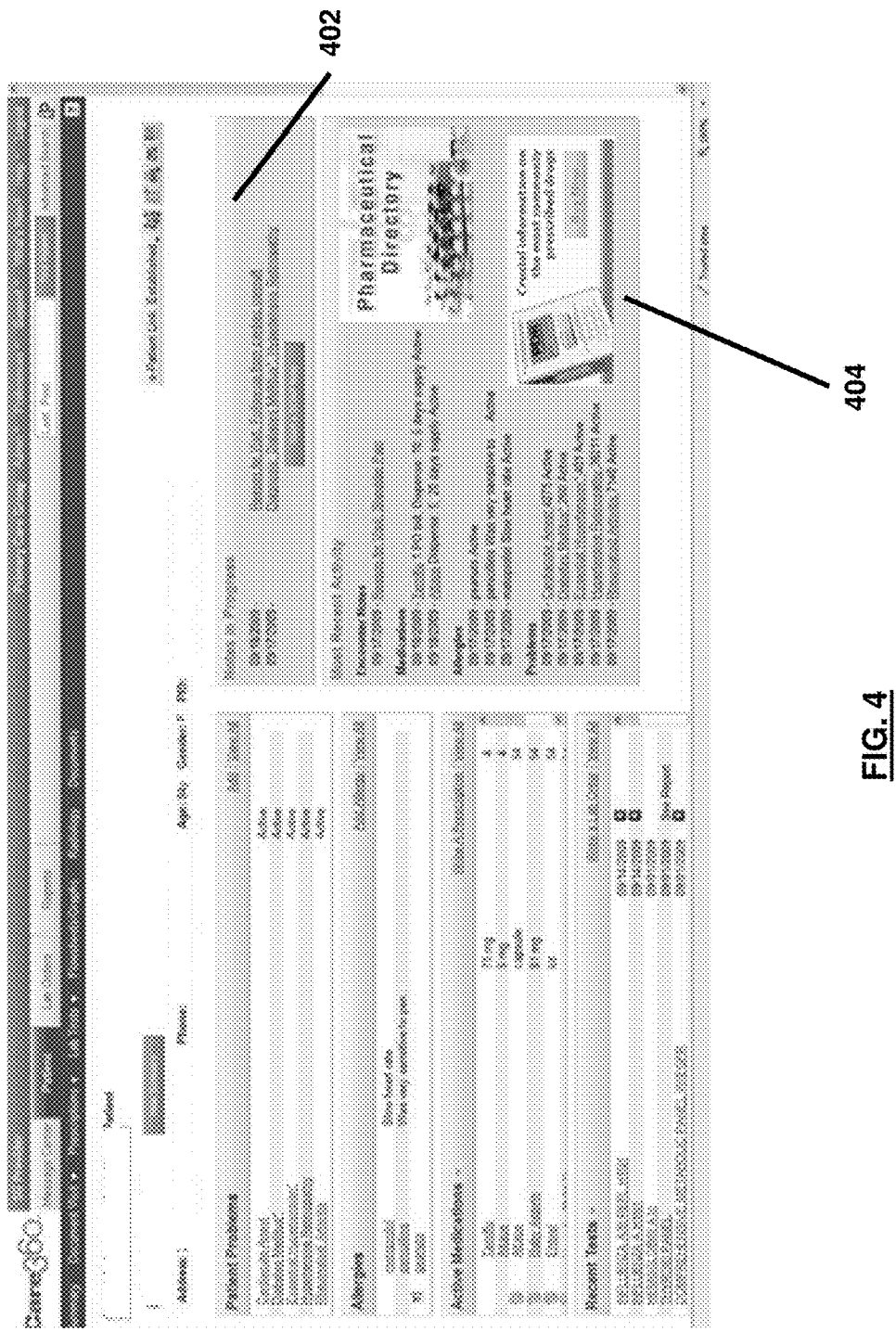
FIGS. 4-6 illustrate exemplary information blocks presented to a user screen associated with an EMR application by an information management server in accordance with an embodiment herein.

FIG. 4, with reference to FIGS. 1 through 3, illustrates exemplary information blocks presented to the user screen 210 associated with the EMR application 208 by the information management server 102 in real time during review of content on the user screen 210 by a user. In the illustrated examples, the user is a healthcare provider such as a physician and the information blocks may be context sensitive to the active patient being viewed by the healthcare provider, application sensitive based on the purpose of the application and user sensitive based on the roles or activities allowed by the user. Therefore, the illustrated information blocks presented by the information management server 102 may be configured so as to be used by a physician through the EMR application 208 and contextually related to the content being browsed or viewed by the physician on the user screen 210 at the time of presentation of the information blocks. For example, the physician may enroll a patient for e-caring solutions during a patient visit through the EMR application 208 using a web page presented on the user screen 210. The physician accordingly may be presented in real time an information block 402 that may facilitate the physician to complete enrolment of the patient for e-caring solutions or may additionally provide knowledge store links for e-caring solutions that might be interesting for the physician to use at that time. The information block 402 may be presented and displayed prominently in real time in EMR pages of the EMR application 208 to support the physician. As shown, in FIG. 4, a physician's desk reference (PDR) widget 404 is displayed on the user screen 208 which may be directly linked to corresponding pages of the third party information sources 106.

Figure 5:
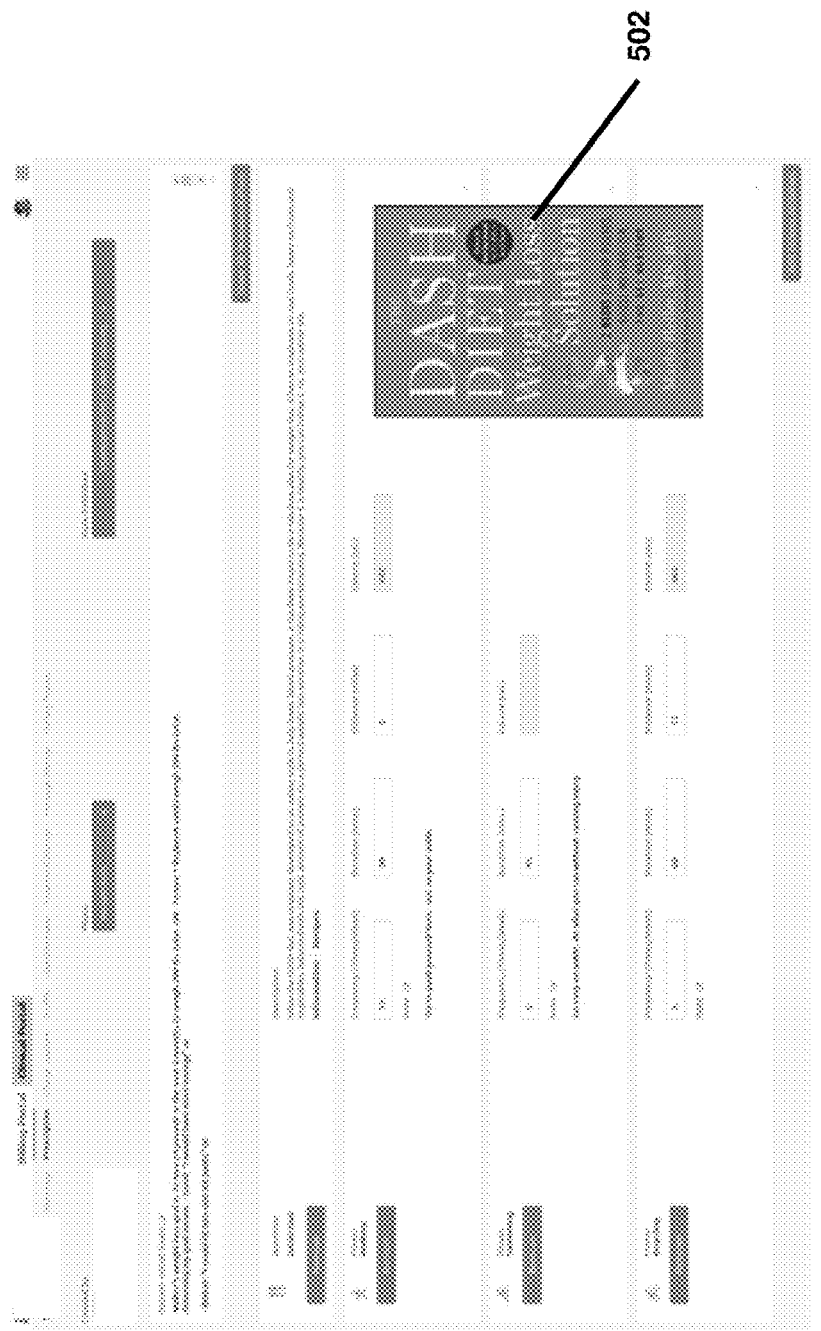

In another example, as illustrated in FIG. 5, with reference to FIGS. 1 through 4, the information management server 102 may present an information block 502 related to diet and weight loss plans on the user screen 210 while writing of a prescription for a weight loss program by the physician so that the physician can view appropriate diet and weight loss plans from the information sources 106 using the information block 502 through the information management server 102.

Figure 6:
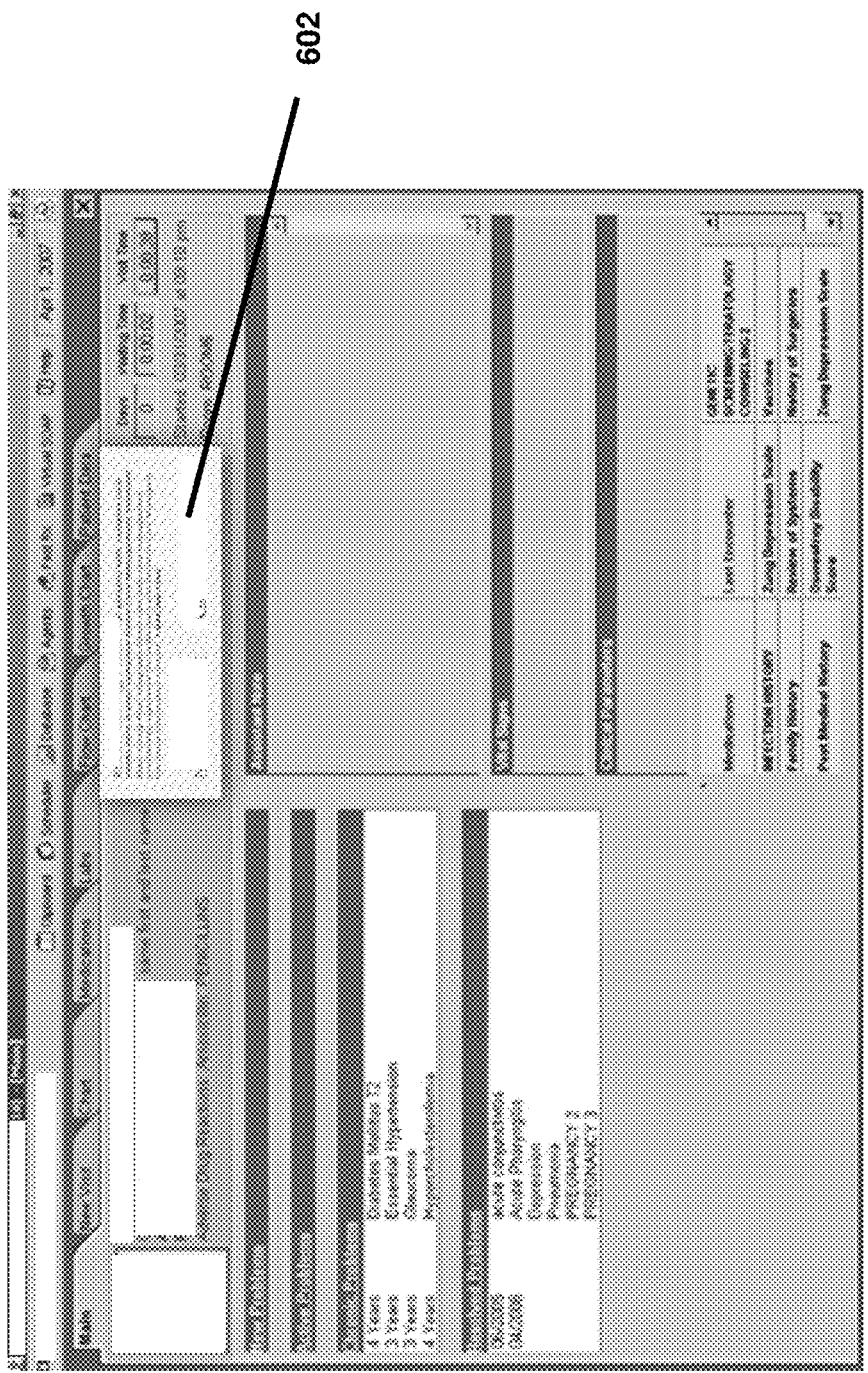

In another example, the information blocks may be configured for use by a patient instead of a healthcare provider. FIG. 6, with reference to FIGS. 1 through 5, illustrates another example of the information blocks presented on the user screen 210 of the EMR application 208 for a patient. For example, an information block 602 as illustrated in FIG. 6 may allow the patient to sign up for e-care solutions by clicking on the information block 602 provided by the information management server 102 and may be directly linked to the third party information sources 106. In an example, multiple information blocks buttons may be listed on the user screen 210 and made available for various patient problems based on the contextual information. These multiple information blocks buttons may be linked directly to simple care websites associated with third party information sources 106 for example. In an example, the patient can view information about medications prescribed by clicking on an information block or a button linked to the information block.

In embodiments, the information management server 102 may facilitate integration of the contextual information associated with the EMR systems 104 or other entities such as medical dashboards, or other medical platforms with the information sources 106. The information blocks may be based on the contextual information provided by the EMR applications such as EMR application 208 through the agent device 204. The information blocks may in an embodiment include widgets. The widgets may be based on the contextual information provided by the EMR application 208 so as to help the users of the EMR system 104a or EMR application 208 such as physicians so as to help them prescribe medications in real time and save physician time. The widgets may for example give the physician immediate access to branded information available in the information management server 102 based on the context sensitive information or context sensitive data.

In an example, the information blocks can be physician information blocks that are delivered to a physician. In another example, the information blocks can be patient information blocks that are delivered to a patient. The patient information blocks may for example include information through widgets for the patient to follow advice received in their doctor office. The patient information blocks may be based on the context sensitive data being presented on the user screen 210 of the EMR application 208 associated with the patient so that the patient can directly access the third party information sources 106 in real time.

The embodiments herein may allow reviewing of internet-based information such as drug information, education information, additional general information, and the like and provide immense value to healthcare providers and patients to make better informed decisions and sooner. The information management server 102 makes the existing healthcare information context sensitive, patient or physician sensitive, and application sensitive by serving up information related to drugs, exercises, health tips, and the like through the information blocks obtained from the third party information sources 106 in context with the information being viewed by the healthcare providers (physicians) or the patients at their EMR applications such EMR application 208.

In an example, the embodiments herein allow to choose widgets from a variety of widgets made available through the information management server 102. The widgets may include such as drugs widgets, patient social data widgets, physician scoring widgets, education widgets, and the like. These widgets show relevant information contextually sensitive to the information that is being viewed by the user such as physician or patient etc.

The embodiments herein may allow pharmacies to reach out to more physicians easily and cost effectively. For example, pharmacies may deliver information on new and existing drugs right in front of the physicians at a precise moment they need it through the information blocks in the form of widgets for example.

The embodiments herein may allow the patients to get health information easily based on their health condition. While patients look through their EMR systems 104, they can be served information from the information sources 106 associated with the third parties or companies that may provide them information based on their health conditions. The patients may not have to search for information based on their health conditions separately. The information management server 102 may allow intelligently serving of the information on the EMR application 208 without the patient requiring going elsewhere for the information.

The embodiments herein allow third party information providers to deliver valid information to their customers at precisely the time the information is consumed at.

In accordance with an embodiment herein, there is provided a system and method for recording patient navigation through different locations or medical spheres or different environments associated with the different independent EMR systems 104 located at different locations with the use of agent devices similar to the agent device 204 and the information management server 102 for security management and surveillance across the independent EMR systems 104. The agent device 204 may for example record patient navigation data in real time. The patient navigation data recorded by the agent device 204 may provide a way to know what the corresponding EMR application 208 of the EMR system 104a is doing. The agent device 204 may transmit the patient navigation data to the information management server 102 and based on the patient navigation data the information management server 102 may know activities of each patient or physician associated with the EMR application 208. The information management server 102 may include a processing circuit 314 (as shown in FIG. 3) that may analyze the patient navigation data for purposes such as patient navigation understanding, patient workflow understanding, security, and surveillance of the patient or physician associated with the EMR application 208. The processing circuit 314 may analyze the patient navigation data for determining inconsistencies in the workflow. For example, if at a particular instant of time, a user such as an administrator is looking at certain patient data through the EMR application 208 by accessing certain pages of the EMR application 208 when the patient is not present or when the patient did not perform any activity with the respective EMR system 104a, the processing circuit 314 may report an inconsistency or a possible breach of security and notify the EMR system 104a or higher authorities. The processing circuit 314 may correlate patient navigation data, user sensitive data, context sensitive data, and application sensitive data obtained from the agent device 204 for performing surveillance in real time.

In an example, a user may create activities associated with a patient when the patient performs tasks such as enters a hospital premise, checks in the hospital room, makes payments, moves to another hospital, visits a doctor, meets another doctor in the same hospital, moves to another environment such as another hospital etc. or moves back to home, and the like whenever an event occurs. The occurrence of events may be recorded by an administrator of the EMR system 104a. The agent device 204 may be configured to review different activities of the patient and occurrence of different events across multi-EMR setup across multi-environment setup and transmit the information to the information management server 102. The processing circuit 314 of the information management server 102 may process the information to perform patient navigation in association with the context sensitive patient data, application sensitive patient data and the user context data pertinent to a patient. The patient processing circuit 314 may, for example, identify whether a patient has gone from one hospital to another, whether the patient has gone back to home, and the like. The processing circuit 314 may build a navigation map in real time that defines movements of the patient or any other associated person between different environments or different locations of the same environment. The agent device 204 residing in the EMR system 104a may track and monitor logging information into the EMR application 208 of the EMR system 104a. For example, if an administrator is logging into the EMR application 208 to view records of a patient, the EMR application 208 may generate a signal that may be recorded by the agent device 204 along with the context sensitive, application sensitive, and the user sensitive information or data at the time of generating the signal. The signal may be treated as a surveillance signal in an example. A variety of such signals may be generated by the EMR application 208 upon occurrence of different events associated with various patient or user activities across multi-EMR, multi-environment spheres. The signals may define a pattern that may be identified by the processing circuit 314 and represented through the navigation map with a representation of the patient movements utilizing the patterns and the sensitive information associated with the patterns. The processing circuit 314 may perform patient navigation by surveillance of the EMR system 104a. For example, there may not be a valid reason for a doctor to look at a patient's record if the patient is not in front of the doctor or if the patient is not admitted in a care unit. There may not be any reason for an administrator to view patient financial records through the EMR system 104a by running the EMR application 208 if the patient has not performed any activity and no such event associated with the patient is monitored recently.

In accordance with the above embodiment, the present invention may provide a computer-implemented surveillance system for monitoring and surveillance of 'Electronic Medical record (EMR) application navigation' through a plurality of navigation interfaces of the EMR application 208. The plurality of navigation interfaces may represent various application instances and screens navigated by a user such as a patient or a healthcare provider or anyone else in a navigation workflow during a workflow event. The workflow event may represent a particular navigation session of the EMR application 208 by the user in a particular environment. Each time the user uses the EMR application 208, a new session may start and may indicate a new workflow event such that the navigation of different workflow tasks during the session may represent the navigation workflow of the workflow event.

The computer-implemented surveillance system may include the EMR system such as the EMR system 104a that includes the EMR application 208. The EMR system 104a is configured to execute computer executable instructions to manage medical records electronically. The surveillance system may include the context-sensitive engine 202 operatively deployed at a front-end of the EMR system 104a. The context-sensitive engine 202 may include the agent device 204 to record EMR application 208 navigation data in real time. The navigation data may include for example various application instances or screens visited by the user during the navigation workflow of the workflow event. The agent device 204 may further record the contextual data comprising application sensitive data, user sensitive data, and the context sensitive data as discussed above in conjunction with various embodiments. The agent device 204 is operatively and communicatively connected with the EMR system 104a. The context engine 202 may further include the installable agent 206 to allow configuration and setup of the agent device 204. The information management server 102 is communicatively connected with the EMR system 104a to facilitate serving of the plurality of information blocks to the EMR system 104a from a plurality of distributed databases in real-time. The databases may be associated with the information sources. The plurality of distributed databases are communicatively connected with the EMR system 104a through the information management server 102.

The transceiver 26 (shown in FIG. 9) may transmit the navigation data and the contextual data from the agent device 204 to the information management server 102. The processing circuit 314 included within or communicatively coupled with the information management server 102 may be configured to analyze the plurality of navigation interfaces associated with the EMR application 208 during the workflow event to generate a signal indicative of analyzed navigation data. The processing circuit 314 is configured to map the analyzed navigation data and the contextual information with actual information pre-stored in a separate database connected with the EMR system 104a. The actual information signifies events occurrences within an environment. For example, if a patient arrives in a medical environment, the actual event occurrence of arrival of the patient in the medical environment may be recorded by the EMR system 104a in the separate database. The processing circuit 314 may be configured to determine an inconsistency in the navigation workflow during the workflow event based on the mapping. For example, if a patient arrives in a medical environment on a particular day, the EMR system 104a may record this as an entry for the event occurrence. If on the same day, a user of the EMR system 104a navigates through medical records of the same patient, there is a high probability that the user is reviewing the record because of a requirement necessitated by the arrival of the patient in the medical environment on that particular day. This reflects a consistency between the actual event occurrence and the navigation workflow. However, if the same patient does not attend the medical environment on the same day, it is unlikely that there would be a requirement to review the medical records of the patient in the EMR system 104a by the user and accordingly an inconsistency may be noted by the processing circuit 314 in this case. A notification device 318 may report the inconsistency to the EMR system 104a. The notification device 318 may generate an electric signal comprising a computer executable file signifying the inconsistency in the navigation workflow during the workflow event. The notification device 318 may then transmit the electric signal, in a network comprising a plurality of communicatively linked data communication devices. The notification device 318 converts the electric signal into a plurality of pixels and displays the plurality of pixels on a display unit 320 to indicate the navigation data and the inconsistency therein.

In an example, the system may include a memory circuit 322 communicatively connected with the EMR system and the information management server 102 to store the recorded EMR application navigation data.

In an embodiment, the processing circuit 314 may further perform analysis of the information blocks delivered to the EMR application 208 in association with the plurality of navigation interfaces associated with the EMR application 208 during a workflow event. The processing circuit 314 may perform mapping of the analyzed information blocks with the actual information pre-stored in the separate database connected with the EMR system 104a. The processing circuit 314 may determine the inconsistency in the navigation workflow during the workflow event based on the mapping of the information blocks with the actual information pre-stored in the separate database about the event occurrences. Since the information blocks are delivered based on the contextual data and the navigation workflow, the information blocks are indicative of the navigation interfaces used by the user. Therefore, the mapping of the delivery of the information blocks with the pre-stored real data is indicative the inconsistency. Likewise discussed above, the notification device may generate the electric signal comprising the computer executable file signifying the inconsistency in the navigation workflow during the workflow event based on situational awareness through the delivery of the information blocks.

The embodiments herein allow multi-EMR and multi-environment patient tracking and surveillance which can allow better security and patient navigation. The embodiments herein allow connecting events and activities at several independent EMR systems 104 in different or same environments occurring together to derive conclusions regarding patient navigation.

Figure 7:
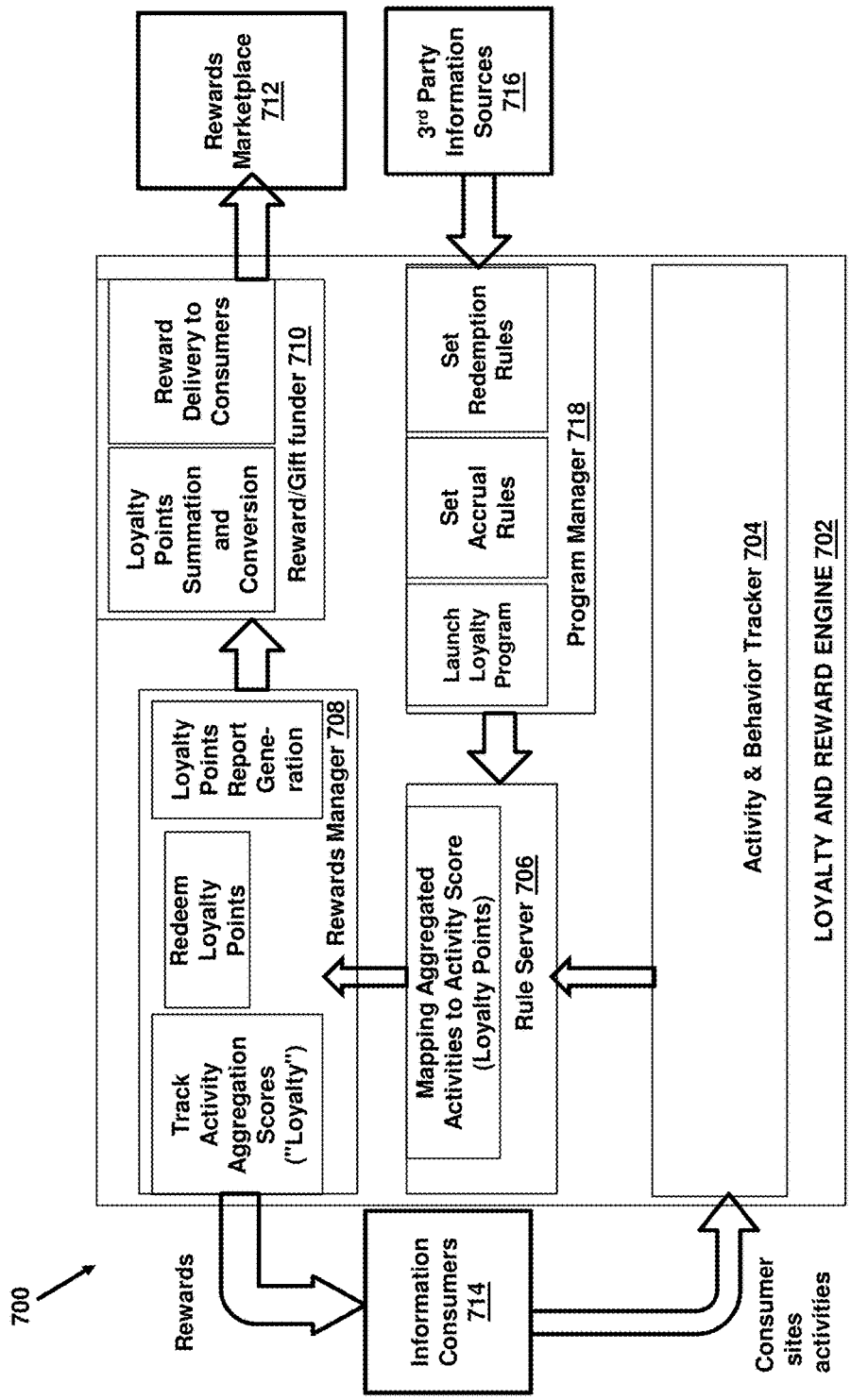
FIG. 7 illustrates an exemplary ecosystem for activity and behavior tracking in accordance with an embodiment herein.

In an example, the embodiments herein may facilitate activity and behavior tracking and accordingly may configure reward and loyalty programs with the use of a loyalty and reward engine 702 such as shown in FIG. 7. FIG. 7, with reference to FIGS. 1 through 6, illustrates an exemplary ecosystem 700 for activity and behavior tracking by the loyalty and reward engine 702 that may be integrated within the information management server 102, in an embodiment. The loyalty and reward engine 702 may allow activity tracking and analysis at the EMR application 208 through an activity and behavior tracker 704 based on which the EMR application 208 users may earn activity scores. The activity and behavior tracker 704 may assign the activity scores based on determining aggregate of various activities. The activity and behavior tracker 702 may be communicatively connected with a rule server 706 that may facilitate mapping of the aggregated activities to activity scores (also referred to as loyalty points). A rewards manager 708 may be connected with the rule server 706. The rewards manager 708 may allow tracking of the activity scores and generating a report based on the tracking of the activity scores. The rewards manager 708 may further facilitate a user to redeem the activity scores. The loyalty and rewards engine 702 may further include a reward or gift funder 710 that may be communicatively coupled with the rewards manager 708. The loyalty and rewards engine 702 may allow summation and conversion of the activity scores and ultimately enable delivery of rewards to consumers or users in the form of such as coupons, schemes, bitcoin, or other currency forms, and the like. The rewards may be delivered directly through a rewards marketplace 712 that facilitates enablement of the ecosystem 700 including the rewards marketplace 712, information consumers 714, and third party information sources 716. The third party information sources 716 and the information consumers 714 can be similar to those discussed above. In an example, the rewards and loyalty engine 702 may further include a program manager 718 such that the program manager 718 may develop various loyalty programs based on which the rewards manager 708 and the rewards funder 710 may reward users in the marketplace 712. The program manager 718 may launch loyalty programs, set accrual rules, set redemption rules, and the like. The program manager 718 may, in an embodiment, be controlled by the third party information sources 716. The program manager 718 may further maintain program templates, manage loyalty programs, maintain points rule, and maintain notification templates, and perform various other functions without limitations. In an example, the embodiments herein may facilitate interactions within a multi-environment setup to generate rewards for the users through the loyalty and reward engine 702. The embodiments herein may facilitate rewards management in a multi-institutional setup wherein the users may be connected with a network through EMR applications similar to the EMR application 208. The loyalty and reward engine 702 may be implemented through a set of APIs configured to perform specific functions to facilitate interactions within the marketplace 712. In an example, users can earn activity scores, bitcoin, real currency, coupons, points or any other form of scores or rewards such as that can be rewarded by an insurance company.

In accordance with some embodiments discussed above, the various systems such as the information management server 102 and methods may allow managing of healthcare data such as but not limited to the information blocks and patient navigation data and the like. The information management server 102 may establish a data file or user profile to whom the data file or data contained therein or information blocks contained therein are served. The information management server 102 may generate an electrical signal that may contain the information blocks for example or other data elements. The signal containing the information blocks may be transmitted from the information management server 102 that may be coupled to a plurality of computing devices hosting the EMR applications similar to the EMR application 208 in a network of the plurality of computing devices. The signal is transmitted along a first selected path of transmission. The signal may be received by a computing device (such as those shown in FIG. 9) comprising a transceiver 26 that is connected communicatively with the information management server 102 over the network 25. A processor or CPU 10 may compare the received signal with the original signal generated by the information management server 102 to determine any differences between the signal as a result of data loss, data change, and data corruption through the various transmissions of the signal. If the difference between the signals is less than or equal to a predetermined threshold amount, then the processor 10 allows the signal to proceed to a pixel conversion process. The computing device may include components and devices to convert the signal into a plurality of pixels that represent the information blocks delivered by the information management server 102. If the difference between the signals is greater than the predetermined threshold, then the processor 10 sends the signal to the transceiver 26 for transmission back to the information management server 102, which then selects a second selected path of transmission of the signal to the computing device. The processor 10 once again compares the received signal with the original signal generated by the information management server 102, and the above process repeats until the difference between the signals is less than or equal to the predetermined threshold amount. The converted pixels may be displayed by the EMR application 208 on a display unit 320 or 23 that may be connected to or included within the computing device. The plurality of computing devices may be EMR system 104 in an embodiment.

Figure 8:
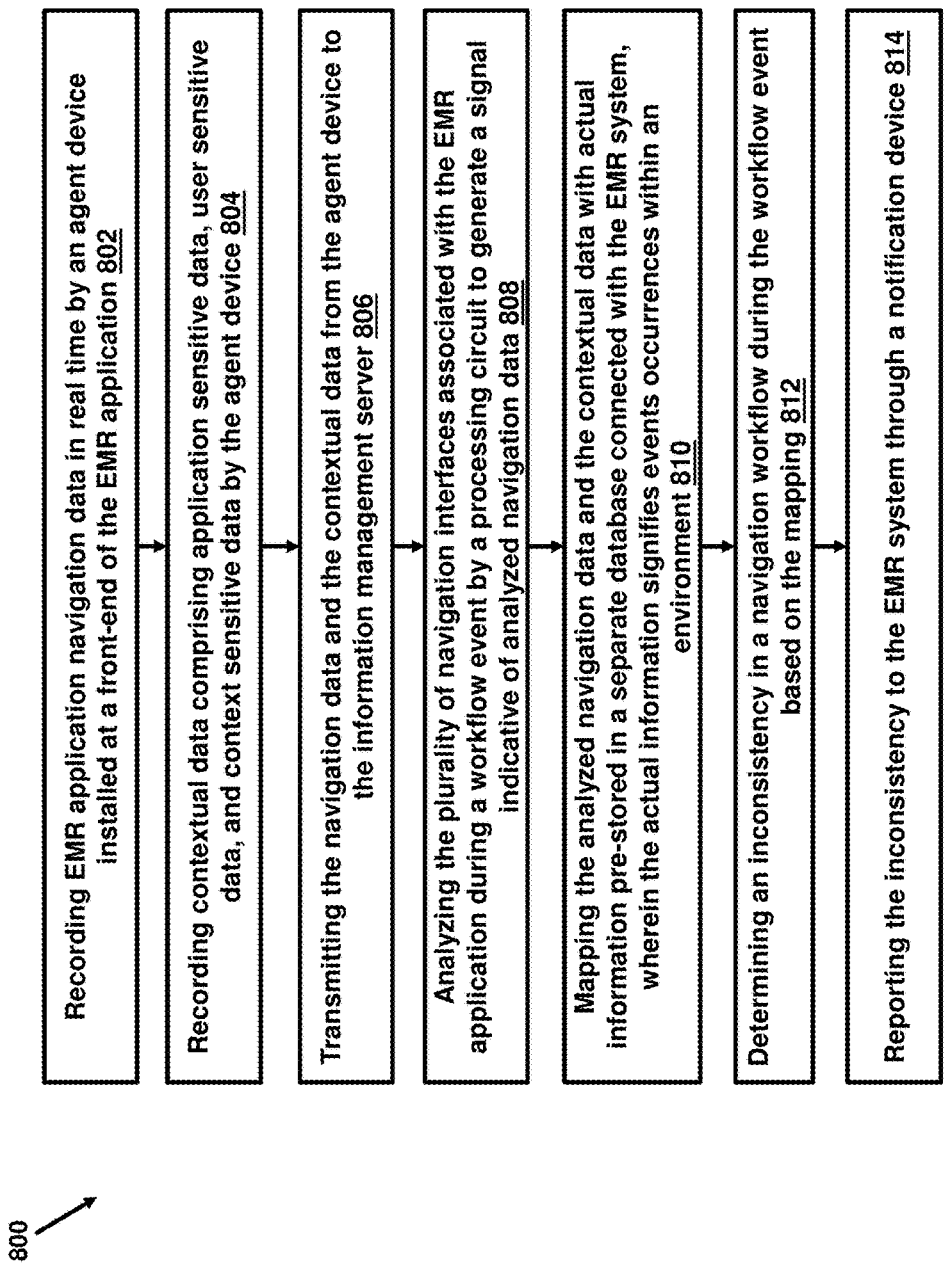
FIG. 8 illustrates a flow chart for a computer-implemented surveillance method for monitoring and surveillance of EMR application navigation.

FIG. 8, with reference to FIGS. 1 through 7, illustrates a flow chart for a computer-implemented surveillance method 800 for monitoring and surveillance of the 'Electronic Medical record (EMR) application navigation' through the plurality of navigation interfaces of the EMR application 208. The method 800 may include, at step 802, recording the EMR application navigation data in real time by the agent device 204 installed at the front-end of the EMR application 208. The method 800 further includes, at step 804, recording the contextual data comprising application sensitive data, user sensitive data, and context sensitive data by the agent device 204. At step 806, the method 800 further includes transmitting the navigation data and the contextual data from the agent device 204 to the information management server 102. At step 808, the method 800 includes analyzing the plurality of navigation interfaces associated with the EMR application 208 during the workflow event by the processing circuit 314 to generate the signal indicative of the analyzed navigation data. At step 810, the method 800 includes mapping the analyzed navigation data and the contextual data with the actual information pre-stored in the separate database connected with the EMR system 104*a*. At step 812, the method 800 includes determining the inconsistency in the navigation workflow during the workflow event based on the mapping. At step 814, the method 800 includes reporting the inconsistency to the EMR system 104*a* through the notification device 318. The step of reporting may include generating the electric signal comprising the computer executable file signifying the inconsistency in the navigation workflow during the workflow event, transmitting the electric signal, in a network comprising a plurality of communicatively linked data communication devices, converting the electric signal into a plurality of pixels, and displaying the plurality of pixels on the display unit 320 to indicate the navigation data and the inconsistency therein.

The method 800 may further include generating a set of information blocks based on the contextual information received from the agent device 204 by the information management server 102. The information blocks may be defined as a patient-centric information block presentable for use by a patient section of the EMR application 208 and/or as a physician-centric information block and presentable for use by a healthcare provider section of the EMR application 208.

The method 800 may further include aggregating a plurality of information pieces from the plurality of distributed databases containing a variety of information types such that the plurality of information pieces are utilized by the information management server 102 to create the plurality of information blocks based on the contextual data and the navigation data. In an embodiment, the information blocks are configured as real time information widgets presentable on a display of the EMR system 104*a*. The presentable real time information widgets are configured based on the plurality of information pieces aggregated by the aggregation engine and the contextual data obtained from the agent device 204.

The method 800 may further include delivering one or more information blocks of the plurality of information blocks on the display unit 320 of the EMR system 104*a* based on the contextual data and the navigation data in real time. The delivered information blocks may be configured as real time information widgets presentable on the display unit 320 of the EMR system 104*a*. The method 800 may further include analyzing the information blocks delivered to the EMR application 208 in association with the plurality of navigation interfaces associated with the EMR application 208 during the workflow event. The method 800 may include mapping of the analyzed information blocks with the actual information pre-stored in the separate database connected with the EMR system 104*a*. The method 800 may further include determining an inconsistency in the navigation workflow during the workflow event based on the mapping of the information blocks with the actual information pre-stored in the separate database about the event occurrences. An electric signal may then be generated such that the electric signal includes a computer executable file signifying the inconsistency in the navigation workflow during the workflow event based on situational awareness through the delivery of the information blocks.

Figure 9:
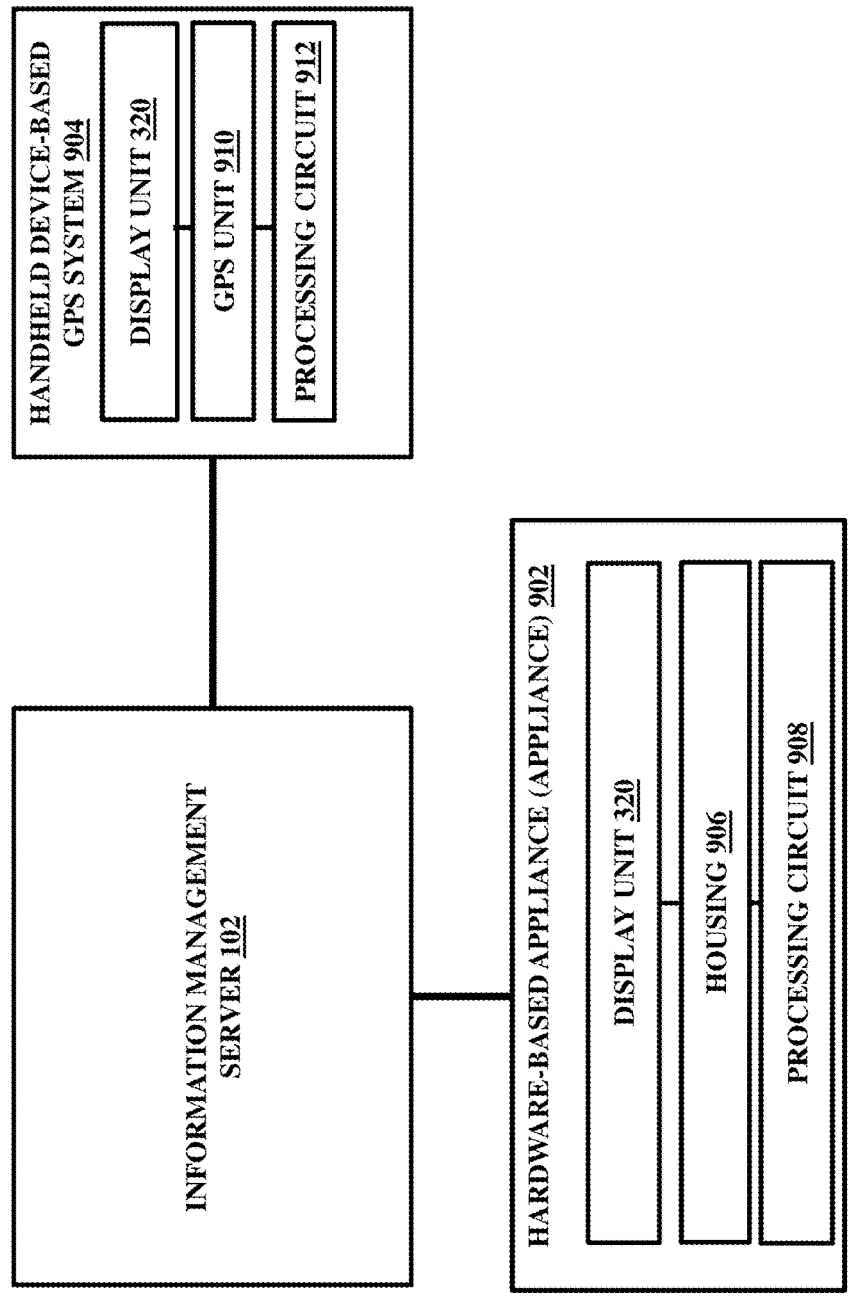
FIG. 9 illustrates an information management server and other connected devices configured as a hardware-based appliance or a kiosk in accordance with an embodiment herein.

FIG. 9, with reference to FIGS. 1 through 8, illustrates the information management server 102 connected to a handheld device-based GPS system 904 and/or a hardware-based appliance 902 such that the present invention for providing navigation-based surveillance may be embodied in the form of a standalone device or a kiosk or a machine or a handheld device or a handheld device-based instrument for monitoring and surveillance purposes. The handheld device-based GPS system 904 may include the display unit 320 such that the inconsistency or any other output generated and transmitted by the information management server 102 may be displayed at the display unit 320. The handheld device-based GPS system 904 may include a GPS unit 910 to generate and sense location information for providing positioning information of a patient. This may facilitate identification of locations of patients in an environment upon event occurrences such that alerts may be setup to receive notifications when a particular patient is noted in an environment and accordingly the event occurrences may be noted and recorded. The event occurrences may be used to compare with the navigation and contextual data obtained from the information management server 102 to identify the inconsistency by the information management server 102 or by the handheld device-based GPS system 904 through an in-built processing circuit 912 for performing custom processing tasks.

The information management server 102 may be communicatively and operatively connected with the hardware-based appliance (hereafter referred to as appliance) 902 such that any output including information about the consistency without limitations generated by the information management server 102 may be displayed on the display unit 320 included within the appliance 902. The appliance 902 may be embodied as a kiosk or a standalone machine or device. The appliance 902 may include the display unit 320 and a housing 906 containing the display unit 320 and other components. The appliance 902 and/or the handheld device-based GPS system 904 may each include the processing circuit 912 to perform one or more tasks at a local level that are otherwise performed by the information management server 102 so that the information management server 102 may transmit the contextual and the navigation data to either the appliance 902 or the handheld device-based GPS system 904 and the processing circuit 908 may execute certain instructions to perform monitoring and surveillance tasks.

In accordance with various embodiments, the information management server 102 is coupled to EMR system such 104*a*. However, in various other embodiments, various other data management systems or records management systems or applications in a healthcare setup or in any other environment may be employed without limitations. In some embodiments, various types of applications such as consumer applications may be used instead of and/or in addition to the EMR system 102a. The consumer applications may be healthcare applications or any other types of applications that may consume the information blocks and may require some level of navigation surveillance. In some embodiments, the applications may be desktop-based applications.

Some of the embodiments herein may be embodied as a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon. Such non-transitory computer readable storage media can be any available media that can be accessed by a special purpose device, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose device to perform a certain function or group of functions. Computer-executable instructions also include program modules that are executed by computers in stand-alone or network environments. Generally, program modules include routines, programs, components, data structures, objects, and the functions inherent in the design of special-purpose devices, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

In an exemplary embodiment, the various modules described herein and illustrated in the figures are embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that are configured with electronic circuits process computer logic instructions capable of providing digital and/or analog signals for performing various functions as described herein. The various functions can further be embodied and physically saved as any of data structures, data paths, data objects, data object models, object files, database components. For example, the data objects could be configured as a digital packet of structured data. The data structures could be configured as any of an array, tuple, map, union, variant, set, graph, tree, node, and an object, which may be stored and retrieved by computer memory and may be managed by processors, compilers, and other computer hardware components. The data paths can be configured as part of a special computer CPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be configured as physical locations in computer memory and can be a variable, a data structure, or a function. In the embodiments configured as relational databases (e.g., such Oracle® relational databases), the data objects can be configured as a table or column. Other configurations include specialized objects, distributed objects, object oriented programming objects, and semantic web objects, for example. The data object models can be configured as an application programming interface for creating HyperText Markup Language (HTML) and Extensible Markup Language (XML) electronic documents. The models can be further configured as any of a tree, graph, container, list, map, queue, set, stack, and variations thereof. The data object files are created by compilers and assemblers and contain generated binary code and data for a source file. The database components can include any of tables, indexes, views, stored procedures, and triggers.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor, and may be configured, for example, as a kiosk.

The embodiments herein can include both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.\

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 10:
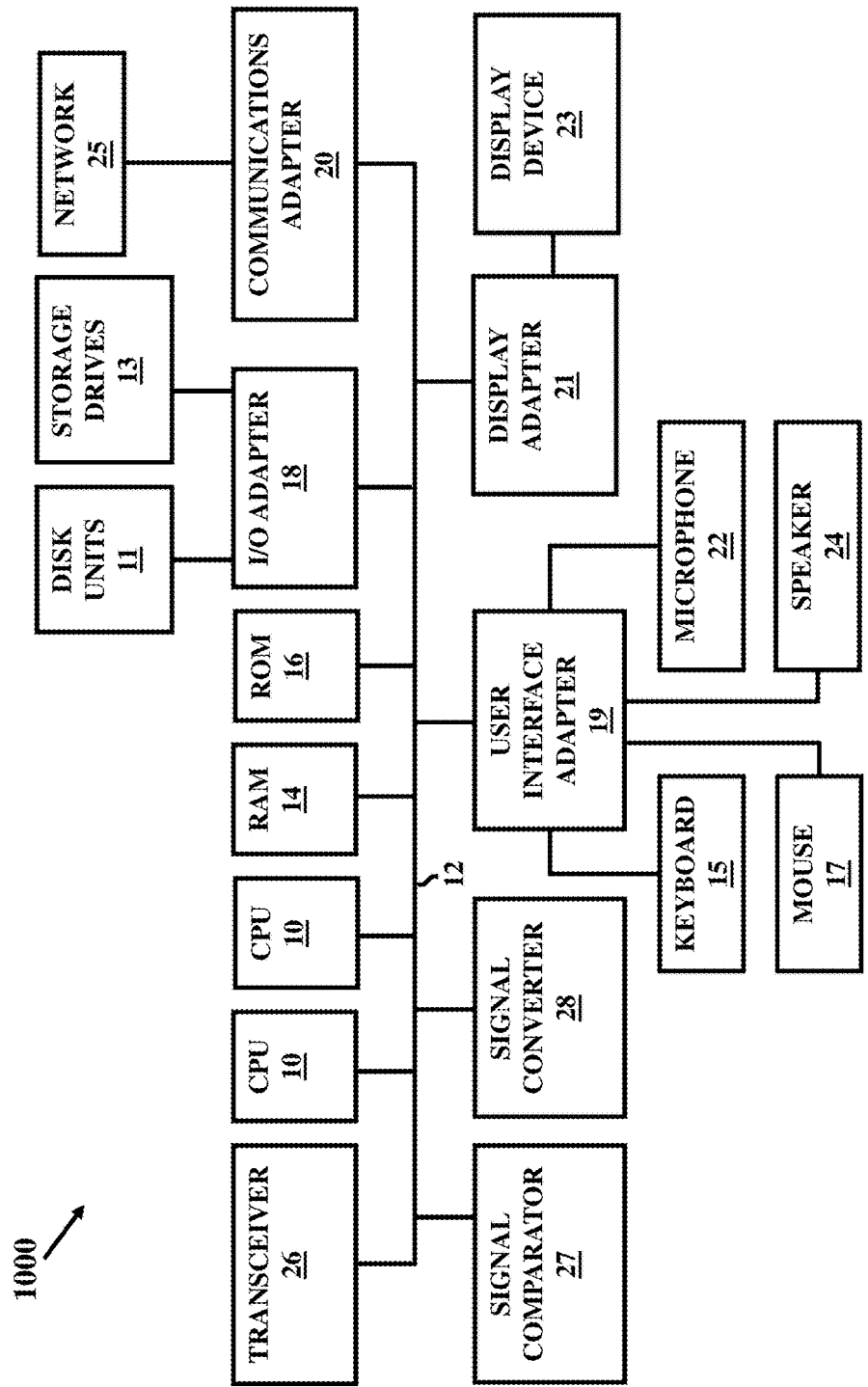
FIG. 10 illustrates a computer system that may be used in accordance with the embodiments herein.

A representative hardware environment for practicing the embodiments herein is depicted in FIG. 10, with reference to FIGS. 1 through 9. This schematic drawing illustrates a hardware configuration of an information handling/computer system 1000 in accordance with the embodiments herein. The system 1000 comprises at least one processing device 10. The special-purpose CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system 1000 can read the inventive instructions on the program storage devices and follow these instructions to execute the methodology of the embodiments herein. The system 1000 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example. Further, a transceiver 26, a signal comparator 27, and a signal converter 28 may be connected with the bus 12 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

I claim:
1. A computer-implemented surveillance system for monitoring and surveillance of Electronic Medical Record (EMR) application navigation through a plurality of navigation interfaces of an EMR application, said system comprising:
   an EMR system comprising said EMR application, wherein said EMR system is configured to execute computer executable instructions to manage computerized medical records electronically;
   a context-sensitive engine operatively deployed at a front-end of said EMR system, said context-sensitive engine comprising:
   an agent device to:
      record EMR application navigation data in real time; and
      record contextual data comprising application sensitive, user sensitive, and context sensitive data,
   wherein said agent device is operatively and communicatively connected with said EMR system;
   an installable computer-executable agent file to allow configuration and setup of said agent device;
   an information management server communicatively connected with said EMR system to facilitate serving of computer executable information blocks to said EMR system from a plurality of distributed databases in real-time, wherein each of said plurality of distributed databases are communicatively connected with said EMR system through said information management server, wherein delivery of said computer executable information blocks is based on said contextual information;
   a transceiver to transmit said navigation data and said contextual data from said agent device to said information management server;
   a processing circuit included within or communicatively coupled with said information management server, wherein said processing circuit:
      analyzes said plurality of navigation interfaces associated with said EMR application during a workflow event to generate a signal indicative of analyzed navigation data;
      maps said analyzed navigation data and said contextual information with actual information pre-stored in a separate database connected with said EMR system, wherein said actual information signifies events occurrences within an environment; and determines an inconsistency in a navigation workflow during said workflow event based on said mapping;

a notification device to report said inconsistency to said EMR system, wherein said notification device:

generates an electric signal comprising a computer executable file signifying said inconsistency in said navigation workflow during said workflow event;

transmits said electric signal in a network comprising a plurality of communicatively linked data communication devices;

converts said electric signal into a plurality of pixels; and displays said plurality of pixels on a display unit to indicate said navigation data and said inconsistency therein, a handheld device-based GPS system comprising:

a second display unit such that an output generated and transmitted by the information management server is displayed at the second display unit;

a GPS unit to generate and sense location information for providing positioning information of an entity, wherein the positioning information is alternatively used to compare said event occurrences with said navigation data and said contextual information obtained from the information management server to identify said inconsistency by said handheld device-based GPS system to prevent user access of said computer executable information blocks in response to said inconsistency and allow user access of said computer executable information blocks in response to a correlation of said navigation data and said contextual information; and an appliance housing containing said second display unit.

2. The system of claim 1, further comprising a memory circuit communicatively connected with said EMR system to store said recorded EMR application navigation data.

3. The system of claim 1, wherein said processing circuit further performs: analyzing of said information blocks delivered to said EMR application in association with said plurality of navigation interfaces associated with said EMR application during a workflow event;

mapping of said analyzed information blocks with said actual information pre-stored in a separate database connected with said EMR system;

determining an inconsistency in a navigation workflow during said workflow event based on said mapping of said information blocks with said actual information pre-stored in said separate database about said event occurrences; and generating an electric signal comprising a computer executable file signifying said inconsistency in said navigation workflow during said workflow event based on situational awareness through said delivery of said information blocks.

4. The system of claim 1, wherein said information management server further comprises an information blocks creator, and wherein said information blocks creator generates a set of information blocks based on said contextual information received from said agent device by said information management server.

5. The system of claim 1, wherein said information management server further comprises an information button knowledge base, and wherein said information button knowledge base configures a widget presentable on said EMR application along with an information block such that said information block presents a limited information to said EMR application and said widget facilitates redirection to a detailed view of said information at a source web page from where said information contained within said information block is aggregated by said information blocks creator.

6. The system of claim 1, wherein said information management server further comprises a plurality of Application Programming Interfaces (APIs) to execute a plurality of custom applications.

7. The system of claim 1, wherein said information management server is configured to generate said information blocks such that said information blocks are defined as at least one of:

a patient-centric information block presentable for use by a patient section of said EMR application; and a physician-centric information block and presentable for use by a healthcare provider section of said EMR application.

8. The system of claim 1, wherein said information management server further comprises an aggregation engine to aggregate a plurality of information pieces from said plurality of distributed databases containing a variety of information types.

9. The system of claim 8, wherein said information blocks are configured as real time information widgets presentable on a display of said EMR system, wherein said presentable real time information widgets are configured based on said plurality of information pieces aggregated by said aggregation engine and said contextual data obtained from said agent device.

10. A computer-implemented surveillance method for monitoring and surveillance of Electronic Medical Record (EMR) application navigation through a plurality of navigation interfaces of an EMR application, said method comprising:

recording EMR application navigation data in real time by an agent device installed at a front-end of said EMR application;

recording contextual data comprising application sensitive data, user sensitive data, and context sensitive data by said agent device, wherein said agent device is operatively and communicatively connected with said EMR system;

transmitting said navigation data and said contextual data from said agent device to said information management server;

analyzing said plurality of navigation interfaces associated with said EMR application during a workflow event by a processing circuit to generate a signal indicative of analyzed navigation data;

mapping said analyzed navigation data and said contextual data with actual information pre-stored in a separate database connected with said EMR system, wherein said actual information signifies events occurrences within an environment;

determining an inconsistency in a navigation workflow during said workflow event based on said mapping; and reporting said inconsistency to said EMR system through a notification device, wherein said reporting comprises:

generating an electric signal comprising a computer executable file signifying said inconsistency in said navigation workflow during said workflow event;

transmitting said electric signal, in a network comprising a plurality of communicatively linked data communication devices;

converting said electric signal into a plurality of pixels; and displaying said plurality of pixels on a display unit to indicate said navigation data and said inconsistency therein, wherein the EMR application is communicatively connected to a handheld device-based GPS system, wherein the handheld device-based GPS system comprises:
   a second display unit such that an output generated and transmitted by the information management server is displayed at the second display unit;
   a GPS unit to generate and sense location information for providing positioning information of an entity, wherein the positioning information is alternatively used to compare said event occurrences with said navigation data and said contextual information to identify said inconsistency by said handheld device-based GPS system to prevent user access of computer executable information blocks in response to said inconsistency and allow user access of said computer executable information blocks in response to a correlation of said navigation data and said contextual information; and
   an appliance housing containing said second display unit.

11. The method of claim 10, further comprising generating a set of the information blocks based on said contextual information received from said agent device by said information management server such that said information blocks are defined as at least one of:
   a patient-centric information block presentable for use by a patient section of said EMR application; and
   a physician-centric information block and presentable for use by a healthcare provider section of said EMR application.

12. The method of claim 10, further comprising aggregating a plurality of information pieces from a plurality of distributed databases containing a variety of information types such that said plurality of information pieces are utilized by said information management server to create a plurality of the information blocks based on said contextual data and said navigation data.

13. The method of claim 12, wherein said information blocks are configured as real time information widgets presentable on a display device of said EMR system, and wherein said presentable real time information widgets are configured based on said plurality of information pieces aggregated by said aggregation engine and said contextual data obtained from said agent device.

14. The method of claim 13, further comprising delivering one or more information blocks of said plurality of information blocks on said display device of said EMR system based on said contextual data and said navigation data in real time, wherein said delivered information blocks are configured as real time information widgets presentable on said display device of said EMR system.

15. The method of claim 14, further comprising:
   analyzing said information blocks delivered to said EMR application in association with said plurality of navigation interfaces associated with said EMR application during a workflow event;
   mapping said analyzed information blocks with said actual information pre-stored in a separate database connected with said EMR system; and
determining an inconsistency in a navigation workflow during said workflow event based on said mapping of said information blocks with said actual information pre-stored in said separate database about said event occurrences; and
   generating an electric signal comprising a computer executable file signifying said inconsistency in said navigation workflow during said workflow event based on situational awareness through said delivery of said information blocks.

\* \* \* \* \*